United States Patent [19]

Ondetti et al.

[11] 4,129,571
[45] Dec. 12, 1978

[54] AMINO ACID DERIVATIVES

[75] Inventors: Miguel A. Ondetti, Princeton; Michael E. Condon, Lawrenceville, both of N.J.

[73] Assignee: E. R. Squibb & Sons, Inc., Princeton, N.J.

[21] Appl. No.: 846,645

[22] Filed: Oct. 31, 1977

Related U.S. Application Data

[62] Division of Ser. No. 759,685, Jan. 17, 1977.

[51] Int. Cl.$^2$ .................. C07D 207/16; C07D 403/12
[52] U.S. Cl. .................. 260/326.2; 546/188; 546/189; 546/221; 546/226; 546/242; 546/245; 260/326.25; 260/326.46; 260/326.47; 560/16; 560/153; 560/147; 424/267; 424/274; 424/309; 424/311
[58] Field of Search ........... 260/326.2, 326.46, 326.25, 260/326.47

[56] References Cited

U.S. PATENT DOCUMENTS

| | | | |
|---|---|---|---|
| 4,046,889 | 9/1977 | Ondetti et al. | 260/326.2 |
| 4,052,511 | 10/1977 | Cushman et al. | 260/239 A |
| 4,064,235 | 12/1977 | Yanaihara et al. | 260/112.5 R |

FOREIGN PATENT DOCUMENTS

| | | | |
|---|---|---|---|
| 2349707 | 4/1974 | Fed. Rep. of Germany | 260/360.7 |
| 51-24490 | 7/1976 | Japan | 260/306.7 |

OTHER PUBLICATIONS

Schmidt et al; Angew Chem., vol. 15, p. 42 (1976).
Pettit; *Synthetic Peptides* vol. 1, pp. 94–104 (1975).
Fu-Chih Huang et al.; J.A.C.S., vol. 97, pp. 3858–3859 (1975).
Adriaens et al.; *Antimicrobial Agnets and Chemotherapy;* 8, pp. 638–642 (1975).
Latruffe et al.; *Biochemie,* vol. 57, pp. 849–857 (1975).
Hausler et al.; Chem. Ber., vol. 107 pp. 145–151 (1974).
Yajima et al.; CA vol. 65: 13819h (1966).
Oparil et al.; New England J. of Med.,vol. 291, p. 289 (1974).
Gavras et al.; New England J. of Med., vol. 291; p. 811 (1974).
Thomas et al.; Chem. Abs., vol. 77 : 33851w (1972).

*Primary Examiner*—Nicholas S. Rizzo
*Assistant Examiner*—Mary C. Lee
*Attorney, Agent, or Firm*—Lawrence S. Levinson; Merle J. Smith

[57] ABSTRACT

New substituted acyl derivatives of amino acids which have the general formula

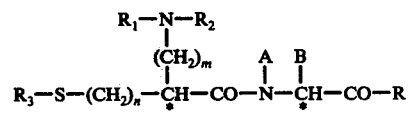

are useful as angiotensin converting enzyme inhibitors.

11 Claims, No Drawings

AMINO ACID DERIVATIVES

This is a division, of application Ser. No. 759,685, filed Jan. 17, 1977.

SUMMARY OF THE INVENTION

This invention relates to new substituted acyl derivatives of amino acids which have the general formula

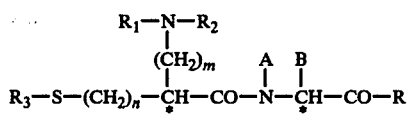

and salts thereof, wherein
R is hydroxy or lower alkoxy;
$R_1$ is hydrogen, lower alkanoyl or amino(imino)methyl;
$R_2$ is hydrogen, lower alkyl or phenyl-lower alkylene;
$R_3$ is hydrogen, lower alkanoyl, benzoyl or

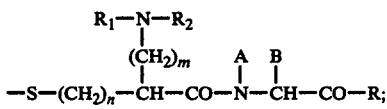

A is hydrogen, lower alkyl or hydroxy-lower alkylene;
B is hydrogen, lower alkyl, phenyl, phenyl-lower alkylene, hydroxy-lower alkylene, hydroxyphenyl-lower alkylene, amino-lower alkylene, guanidino-lower alkylene, mercapto-lower alkylene, lower alkyl-thio-lower alkylene, imidazolyl-lower alkylene, indolyl-lower alkylene, carbamoyl-lower alkylene or carboxy-lower alkylene;
or A and B together form a $(CH_2)_p$ bridge which completes a ring of 5 or 6 atoms with the nitrogen and carbon to which they are joined, one carbon optionally bearing a hydroxy group;
n is 0 or 1;
m is 0, 1, 2, 3 or 4; at least one of m and n is other than 0; and
p is 3 or 4.
The asterisks denote centers of asymmetry.

DETAILED DESCRIPTION OF THE INVENTION

The invention in its broad aspects includes substituted acyl derivatives of amino acids having formula I above. The substituted acyl groups refer to the side chains on the carbon beta to the nitrogen atom. The one side chain has one or two sulfur containing groups and the second side chain has one nitrogen containing group. Within the class defined by formula I, because of their properties, certain subgroups are preferred.

Compounds in the group represented by formula I which are derived from or include the structure of the amino acids glycine, alanine, leucine, threonine, phenylalanine, lysine, arginine, glutamine, histidine, methionine, serine, cysteine, tyrosine, valine, asparagine, glutamic acid, proline, hydroxyproline, phenylglycine or tryptophane are broadly preferred. Preferred modifications are compounds of formula I wherein R is hydroxy; $R_1$ is hydrogen, lower alkanoyl or amino(imino)methyl [particularly hydrogen, methyl, acetyl or amino(imino)methyl]; $R_2$ is hydrogen, lower alkyl (particularly hydrogen or methyl) or phenyl-lower alkylene (particularly benzyl), most particularly $R_2$ is hydrogen; $R_3$ is hydrogen, lower alkanoyl or benzoyl (particularly hydrogen, or acetyl); A is hydrogen; B is lower alkyl, guanidino-lower alkylene (particularly guanidinopropyl), amino-lower alkylene (particularly amino-$C_3$-$C_4$-lower alkylene) or phenyl-lower alkylene (particularly phenylmethyl); or A and B complete a 5- or 6-membered ring; m is 0, 3 or 4 and n is 0 or 1, but not both m and n are 0.

Especially preferred are those compounds of formula I which are derived from proline and have the formula

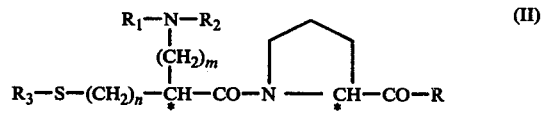

The symbols have the same preferred meanings described above.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkylene groups are of the same kind also having 1 to 7 carbons. Similarly, the lower alkoxy groups are of the same kind with a link to oxygen, for example, methoxy, ethoxy, propoxy, isopropoxy, butoxy, isobutoxy, t-butoxy and the like. The $C_1$-$C_4$ members, especially $C_1$ and $C_2$ members, of all types are preferred. Phenylmethyl is the preferred phenyl-lower alkylene group and methoxy and t-butoxy the preferred lower alkoxy groups. The lower alkanoyl groups are the acyl radicals of the lower (up to 7 carbons) fatty acids, e.g., acetyl, propionyl, butyryl and the like, acetyl being preferred.

The amino(imino)methyl group represented by $R_1$ is the residue of the guanidino radical

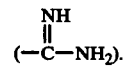

The products of formula I and the preferred subgroups can be produced by various methods of synthesis. According to a preferred method, the amino acid of the formula

wherein A and B are defined as above, and R is hydroxy, is acylated with an acid of the formula

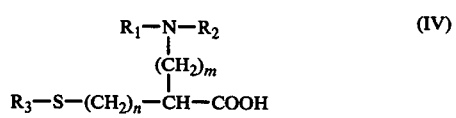

wherein $R_1$ is an acyl group, and $R_2$, $R_3$, m and n have the meaning defined above, by one of the known procedures in which the acid IV is activated, prior to reaction with the amino acid III, involving formation of a mixed anhydride, symmetrical anhydride, acid chloride, active ester, Woodward reagent K, N,N'-carbonylbisimidazole, EEDQ (N-ethoxycarbonyl-2-ethoxy-1,2-dihydroquinoline) or the like. When R is lower alkoxy, this or other known methods of coupling such moieties can be used [For a review of these methods, see Methoden der Organischen Chemie (Houben-Weyl) Vol. XV, parts 1 and 2 (1974)].

When the product obtained is an ester, e.g., R is t-butoxy, the ester can be converted to the free carboxy group (R is hydroxy) by cleavage with acids, e.g., trifluoroacetic acid. Conversely the free acid can be esterified by conventional procedures.

Starting materials of formula IV wherein m is 0 are derivatives of the amino acid cysteine which can be produced by known procedures.

The acids of formula IV wherein m is 2, 3 or 4 can be synthesized, according to a preferred method, by the addition of a thiol acid to the substituted acrylic acid of the formula

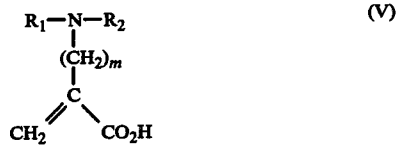
(V)

The latter are obtained by hydrolysis, e.g., with 6N hydrochloric acid, of the methylene lactams of the formula

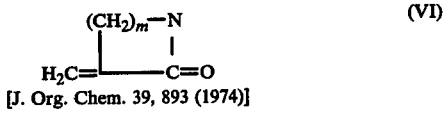
(VI)

[J. Org. Chem. 39, 893 (1974)]

The compounds of formula I wherein m is 1 are obtained by the Curtius rearrangement of an acid of the formula

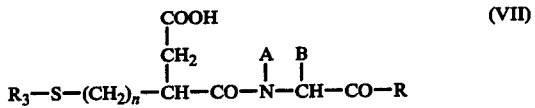
(VII)

The preferred method for producing compounds of formula I wherein n is 0 is by displacement of the halo derivative of the formula

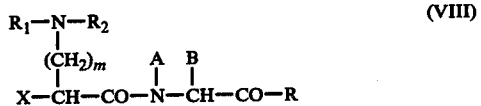
(VIII)

wherein X is halogen, preferably chlorine or bromine, with the thiol acid $R_3$—COSH.

The disulfides of formula I, wherein $R_3$ is

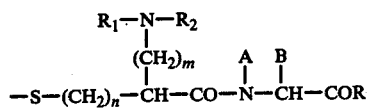

are obtained by oxidation of the compound of the formula

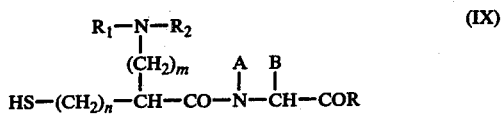
(IX)

e.g., with an alcoholic solution of iodine.

The compounds of formula I wherein $R_1$ is amino(imino)methyl are obtained by reacting a compound of formula I wherein $R_1$ or $R_2$ is hydrogen with a guanyl-forming reagent e.g., guanyl-3,5-dimethylpyrazole nitrate, S-methylisothiourea, or O-methylisourea.

Products of formula I have two asymmetric carbon atoms. These carbon atoms are indicated by an asterisk in formula I. The compounds accordingly exist in diastereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form.

The compounds of formula I form salts which are also part of this invention. The salts include acid-addition salts which are formed by reaction with a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate.

The salts are formed in conventional manner by reacting the free form of the product with one or more equivalents of the appropriate acid or base providing the desired anion or cation in a solvent or medium in which the salt is insoluble, or in water and removing the water by freeze drying. By neutralizing the salt with an insoluble acid like a cation exchange resin in the hydrogen form [e.g., polystyrene sulfonic acid resin .— Dowex 50 (Mikes, Laboratory Handbook of Chromatographic Methods (Van Nostrand, 1961) page 256] eluting with a volatile buffer (e.g. pyridine-acetic acid) and extraction with an organic solvent, the free form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats, dogs, etc. The compounds of this invention intervene in the angiotensinogen → angiotensin I → angiotensin II sequence by inhibiting angiotensin converting enzyme and reducing or eliminating the formation of the pressor substance angiotensin II.

The inhibition of the angiotensin converting enzyme by compounds of formula I can be measured in vitro with isolated angiotensin converting enzyme from rabbit lungs following the procedure described by Cushman and Cheung [Biochem. Pharmacol., 20, 1637 (1971)], and with an excised smooth muscle assay [E. O'Keefe, et al., Federation Proc. 31, 511 (1972)] in which these compounds have been shown to be powerful inhibitors of the contractile activity of angiotensin I and potentiators of the contractile activity of bradykinin.

The administration of a composition containing one or a combination of compounds of formula I or physiologically acceptable salt thereof to the species of hypertensive mammal alleviates or reduces hypertension. A single dose, or preferably two to four divided daily doses, provided on a basis of about 5 to 1000 mg. per kilogram per day, preferably about 10 to 500 mg. per kilogram per day is appropriate to reduce blood pressure. The animal model experiments described by S. L. Engel, T. R. Schaeffer, M. H. Waugh and B. Rubin, Proc. Soc. Exp. Biol. Med. 143, 483 (1973) serve as a useful guide.

The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solution or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. All temperatures are in degrees celsius.

EXAMPLE 1

N-tert-Butyloxycarbonyl-S-p-methoxybenzyl-D-cysteinyl-L-proline tert-butyl ester To a solution of L-proline tert-butyl ester (0.85 g) and hydroxybenzotriazole (0.67 g) in methylene chloride (10 ml) chilled in an ice bath, dicyclohexylcarbodiimide (1.03 g) and N-tert-butyloxycarbonyl-S-p-methoxybenzyl-D-cysteine (1.7 g) are added in that order. After 15 minutes, the ice bath is removed and the mixture is stirred at room temperature overnight. The precipitate is filtered off and the filtrate is washed with 10% potassium bisulfate, water, saturated sodium bicarbonate, and water. The organic phase is dried and concentrated to dryness in vacuo to give N-tert-butyloxycarbonyl-S-p-methoxybenzyl-D-cysteinyl-L-proline tert-butyl ester as an oil. $R_f=0.2$ (silica gel, chloroform).

EXAMPLE 2

D-Cysteinyl-L-proline acetate

To a solution of N-tert-butyloxycarbonyl-S-p-methoxybenzyl-D-cysteinyl-L-proline tert-butyl ester (1.8 g) and anisole (4.4 ml) in dichloromethane (8 ml) chilled in an ice bath, trifluoromethane sulfonic acid (6.0 g) is added. The ice bath is removed and the mixture is stirred at room temperature for 30 minutes. The dichloromethane is removed in vacuo and the residue is triturated with hexane (2 × 200 ml). The residue is dissolved in water and extracted twice with ether. The aqueous phase is applied to a column of 200 ml of cation exchange resin [Dowex 50] in the hydrogen cycle. The column is washed with water until no more acidic material is eluted. The D-cysteinyl-L-proline acetate is eluted with a pyridine-acetic acid buffer pH 6.5, yield 0.66 g. $R_f=0.38$ (silica gel, chloroform:methanol:acetic acid:water).

EXAMPLE 3

N,S-Diacetyl-DL-cysteinyl-L-proline tert-butyl ester

By substituting N,S-diacetyl-DL-cysteine for the N-tert-butyloxycarbonyl-S-p-methoxybenzyl-D-cysteine in the procedure of Example 1, N,S-diacetyl-DL-cysteinyl-L-proline tert-butyl ester is obtained. $R_f=0.25$ (silica gel, ethyl acetate).

EXAMPLE 4

N,S-Diacetyl-DL-cysteinyl-L-proline

N,S-Diacetyl-DL-cysteinyl-L-proline tert-butyl ester (1.9 g) is dissolved in a mixture of anisole (6 ml) and trifluoroacetic acid (12 ml) and the solution is stored at room temperature for 1 hour. The solvents are removed in vacuo and the residue is precipitated from ethyl acetate-ether-hexane, to obtain N,S-diacetyl-DL-cysteinyl-L-proline, yield 1.08 g, m.p. 80°–140°.

EXAMPLE 5

N-Acetyl-DL-cysteinyl-L-proline

N,S-Diacetyl-DL-cysteinyl-L-proline (0.3 g) is dissolved in a mixture of water (4 ml) and concentrated ammonia (4 ml) under a blanket of argon. The solution is stored for 30 minutes at room temperature, saturated with sodium chloride and extracted with ethyl acetate and chloroform. The organic layers are pooled and concentrated to dryness in vacuo to obtain N-acetyl-DL-cysteinyl-L-proline, yield 0.1 g, $R_f=0.25$ (silica gel; benzene:acetic acid, 75:25).

EXAMPLE 6

Methyl N-(p-methoxybenzyl)nipecotate hydrochloride

A mixture of 23 g of methyl nipecotate, 24.3 g of potassium carbonate, and 52 g of p-methoxybenzyl trichloroacetate in 800 ml of toluene is refluxed under nitrogen for 72 hours. The mixture is cooled, the toluene removed in vacuo, the residue dissolved in chloroform, and this solution washed once with 400 ml of aqueous potassium carbonate and then with 400 ml of 10% hydrochloric acid. The chloroform solution is dried and concentrated in vacuo to a viscous brown oil. Trituration of this oil with ethyl acetate affords 30.7 g of methyl N-(p-methoxybenzyl)nipecotate hydrochloride as an off-white crystalline solid. Recrystallization from ethyl acetate yields the analytical sample, m.p. 150°–154°.

EXAMPLE 7

1-(p-Methoxybenzyl)-3-methylene-2-piperidone

A solution of methyl N-(p-methoxybenzyl)nipecotate hydrochloride (30.7 g) and 8.4 g of sodium hydroxide in 900 ml of methanol and 45 ml of water is stirred at room temperature for 17 hours. The solution is evaporated to dryness in vacuo, the residue diluted with toluene, and this again evaporated to dryness in vacuo. To the residue is added 1 liter of acetic anhydride and 140 ml of triethylamine, and the resulting mixture is heated under reflux for 4 hours. The reaction mixture is evaporated to dryness in vacuo, the residue taken up in chloroform, washed with water, dried, and concentrated in vacuo. The residual oil is chromatographed on silica gel using 1:1 hexane-ethyl acetate as the eluant, and yields 16.9 g of 1-(p-methoxybenzyl)-3-methylene-2-piperidone as a chromatographically pure yellow oil. Alternatively, the oil can be distilled to give analytically pure 1-(p-methoxybenzyl)-3-methylene-2-piperidone, b.p. 145°–155°/0.05 mm.

EXAMPLE 8

3-Methylene-2-piperidone

A solution of 1-(p-methoxybenzyl)-3-methylene-2-piperidone (16.9 g) and 21.3 g of anisole in 400 ml of trifluoroacetic acid is refluxed under nitrogen for 48 hours. The solution is evaporated to dryness in vacuo, and the residue chromatographed on 900 g of silica gel using ethyl acetate as eluant, yielding 6.5 g of 3-methylene-2-piperidone as a crystalline solid.

EXAMPLE 9

2-Methylene-5-aminopentanoic acid hydrochloride

A solution of 2.6 g of 3-methylene-2-piperidone in 150 ml of 6N hydrochloric acid is refluxed for 24 hours. The cooled solution is extracted with chloroform, and the aqueous layer concentrated in vacuo to 3.8 g of glassy foam. The foam is heated with methanol, filtered through Celite (diatomaceous earth clarifying agent) to remove a small amount of insoluble material, and the filtrate is evaporated to dryness in vacuo, yielding 2.5 g of 2-methylene-5-aminopentanoic acid hydrochloride as a tan crystalline solid. Recrystallization from isopropanol gives the analytical sample, m.p. 138°–144°.

EXAMPLE 10

2-Methylene-5-(p-methoxybenzyloxycarbonyl)aminopentanoic acid

To a solution of 8.8 g of 2-methylene-5-aminopentanoic acid hydrochloride in 100 ml of water is added with stirring 6.36 g of magnesium oxide, followed by a solution of 12.2 g of p-methoxybenzyloxycarbonyl azide in 100 ml of dioxane, and the resulting mixture is stirred at room temperature for 2 days. The reaction mixture is filtered, and the filtrate diluted with 200 ml of ethyl acetate, two equivalents of Dowex 50 ion exchange resin is added, and the mixture is stirred at room temperature for 2 hours. The resin is then filtered off and washed with water. The layers in the filtrate are separated and the aqueous layer is extracted twice with ethyl acetate. The combined organic layers are dried and concentrated in vacuo to give 18.2 g of 2-methylene-5-(p-methoxybenzyloxycarbonyl)aminopentanoic acid as an amber oil which crystallizes on standing. This is used without further purification.

EXAMPLE 11

2-Acetylthiomethyl-5-(p-methoxybenzyloxycarbonyl)aminopentanoic acid

A solution of 2-methylene-5-(p-methoxybenzyloxycarbonyl)amino pentanoic acid (53 mmoles) in 50 ml of thiolacetic acid is allowed to stand at room temperature for 48 hours. The solution is evaporated to dryness in vacuo, and the residue taken up in chloroform and applied to a silica gel column (700 g). Elution with 5% methanol in chloroform affords 14.2 g of 2-acetylthiomethyl-5-(p-methoxybenzyloxycarbonyl)aminopentanoic acid as an oil. Treatment of this oil with one equivalent of dicyclohexylamine in ether, followed by recrystallization from ethyl acetate affords the corresponding dicyclohexylamine salt, m.p. 112°–114°.

EXAMPLE 12

2-Acetylthiomethyl-5-(p-methoxybenzyloxycarbonyl)aminopentanoic acid N-hydroxysuccinimide ester To a solution of 3.7 g of 2-acetylthiomethyl-5-(p-methoxybenzyloxycarbonyl)aminopentanoic acid and 1.21 g of N-hydroxysuccinimide in 60 ml of dichloromethane at 0°–5° is added 2.16 g of N,N'-dicyclohexylcarbodiimide over 20 minutes with stirring. The resulting mixture is stirred overnight at 0°–5°. The precipitated dicyclohexylurea is filtered off, the filtrate concentrated in vacuo and the residue taken up in ethyl acetate and washed through a silica gel column to give 4.6 g of 2-acetylthiomethyl-5-(p-methoxybenzyloxycarbonyl)amino pentanoic acid N-hydroxysuccinimide ester as an oil, which crystallizes on trituration with ether. Recrystallization from ethyl acetate-hexane affords the analytical sample, m.p. 85°–87°.

EXAMPLE 13

1-[(2-Acetylthiomethyl-5-(p-methoxybenzyloxycarbonylamino)-pentanoyl)]-L-proline tert-butyl ester By substituting 2-acetylthiomethyl-5-(p-methoxybenzyloxycarbonylamino)pentanoic acid for the N-tert-butyloxycarbonyl-S-p-methoxybenzyl-D-cysteine in the procedure of Example 1, 1-[2-acetylthiomethyl-5-(p-methoxybenzyloxycarbonylamino)pentanoyl]-L-proline tert-butyl ester is obtained.

EXAMPLE 14

1-(2-Acetylthiomethyl-5-aminopentanoyl)-L-proline trifluoroacetate

1-[2-Acetylthiomethyl-5-(p-methoxybenzyloxycarbonylamino)pentanoyl]-L-proline tert-butyl ester (2 g) is dissolved in a mixture of trifluoroacetic acid (15 ml) and anisole (6 ml). The solution is stored at room temperature for 1 hour, the solvents are removed in vacuo and the residue is precipitated from ethyl acetate-ether to yield 1-(2-acetylthiomethyl-5-aminopentanoyl)-L-proline trifluoroacetate.

EXAMPLE 15

1-(5-Amino-2-mercaptomethylpentanoyl)-L-proline 1-(2-Acetylthiomethyl-5-aminopentanoyl)-L-proline trifluoroacetate (1 g) is dissolved in a mixture of water (12 ml) and concentrated ammonia (12 ml) under a blanket of argon. The solution is stored 20 minutes at room temperature concentrated to 5 ml and applied to a column of Dowex 50 ion exchange resin in the hydrogen cycle. The column is washed with water and 1-(5-amino-2-mercaptomethylpentanoyl)-L-proline is eluted with a buffer of pyridine-acetic acid at pH 6.5.

EXAMPLE 16

2-Methylene-4-methylaminobutanoic acid hydrochloride

By substituting 1-methyl-3-methylene-2-pyrrolidinone [J. Org. Chem., 39, 893 (1974)] for the 3-methylene-2-piperidone in the procedure of Example 9, 2-methylene-4-methylaminobutanoic acid hydrochloride is obtained.

EXAMPLE 17

2-Methylene-4-(N-p-methoxybenzyloxycarbonyl-N-methylamino)-butanoic acid

By substituting 2-methylene-4-methylaminobutanoic acid hydrochloride for the 2-methylene-5-aminopentanoic acid hydrochloride in the procedure of Example 10, 2-methylene-4-(N-p-methoxybenzyloxycarbonyl-N-methylamino)-butanoic acid is obtained.

EXAMPLE 18

2-Acetylthiomethyl-4-(N-p-methoxybenzyloxycarbonyl-N-methylamino)butanoic acid

By substituting 2-methylene-4-(N-p-methoxybenzyloxycarbonyl-N-methylamino)butanoic acid for the 2-methylene-5-(p-methoxybenzyloxycarbonylamino)-pentanoic acid in the procedure of Example 11, 2-acetylthiomethyl-4-(N-p-methoxybenzyloxycarbonyl-N-methylamino)butanoic acid is obtained.

EXAMPLE 19

1-(4-Amino-2-mercaptomethylbutanoyl)-L-proline

By substituting 2-acetylthiomethyl-4-(N-p-methoxybenzyloxycarbonyl-N-methylamino)butanoic acid for the N-tert-butyloxycarbonyl-S-p-methoxybenzyl-D-cysteine in the procedure of Example 1, and then submitting the product to the procedures of Examples 14 and 15, 1-(2-acetylthiomethyl-4-(N-p-methoxybenzyloxycarbonyl-N-methylamino)butanoyl)-L-proline tert-butyl ester, 1-(2-acetylthiomethyl-4-aminobutanoyl)-L-proline trifluoroacetate, and 1-(4-amino-2-mercaptomethylbutanoyl)-L-proline are obtained.

EXAMPLE 20

2-Acetylthiomethyl-6-(N-methyl-N-acetylamino)hexanoic acid

By substituting 6-(N-methyl-N-acetylamino)-2-methylene hexanoic acid for the 2-methylene-5-(p-methoxybenzyloxycarbonylamino)pentanoic acid in the procedure of Example 11, 2-acetylthiomethyl-6-(N-methyl-N-acetylamino)hexanoic acid is obtained.

EXAMPLE 21

1-[(2-Mercaptomethyl-6-(N-methyl-N-acetylamino)-hexanoyl]-L-proline

By substituting 2-acetylthiomethyl-6-(N-methyl-N-acetylamino)hexanoic acid for the N-tert-butyloxycarbonyl-S-p-methoxybenzyl-D-cysteine in the procedure of Example 1, and then submitting the product to the procedure of Examples 14 and 15, 1-[2-acetylthiomethyl-6-(N-methyl-N-acetylamino)hexanoyl]-L-proline tert-butyl ester, 1-[2-acetylthiomethyl-6-(N-methyl-N-acetylamino)hexanoyl]-L-proline, and 1-[2-mercaptomethyl-6-(N-methyl-N-acetylamino)hexanoyl]-L-proline are obtained.

EXAMPLE 22

1-(5-Guanidino-2-mercaptomethylpentanoyl)-L-proline

A solution of 1-(5-amino-2-mercaptomethylpentanoyl)-L-proline (2.3 g), guanyl-3,5-dimethylpyrazole nitrate (2.41 g) and triethylamine (3.36 ml) in dimethylformamide (20 ml) is stored at room temperature under a blanket of argon for 16 hours. The solvents are removed in vacuo, the residue is dissolved in 0.1 N hydrochloric acid (10 ml) and zinc dust (500 mg) is added. The suspension is stirred at room temperature for 2 hours. After filtering, the filtrate is applied to a column of Dowex 50 ion exchange resin in the hydrogen cycle. The column is washed with water until no more acid is eluted and 1-(5-guanidino-2-mercaptomethylpentanoyl)-L-proline is then eluted with a pyridine-acetate buffer at pH 6.5.

EXAMPLE 23

N-(5-Amino-2-mercaptomethylpentanoyl)glycine

By substituting glycine tert-butyl ester for the proline tert-butyl ester in the procedure of Example 13, and then submitting the product to the procedures of Examples 14 and 15, N-[2-acetylthiomethyl-5-(p-methoxybenzyloxycarbonylamino)pentanoyl]glycine tert-butyl ester, N-[2-acetylthiomethyl-5-aminopentanoyl]glycine and N-(5-amino-2-mercaptomethylpentanoyl)glycine are obtained.

EXAMPLE 24

N-(5-Amino-2-mercaptomethylpentanoyl)-L-leucine

By substituting L-leucine tert-butyl ester for the proline tert-butyl ester in the procedure of Example 13, and then submitting the product to the procedures of Examples 14 and 15, N-[2-acetylthiomethyl-5-(p-methoxybenzyloxycarbonylamino)pentanoyl]-L-leucine tert-butyl ester, N-[2-acetylthiomethyl-5-aminopentanoyl]-L-leucine and N-(5-amino-2-mercaptomethylpentanoyl)-L-leucine are obtained.

EXAMPLE 25

N-(5-Amino-2-mercaptomethylpentanoyl)-L-phenylalanine

By substituting L-phenylalanine tert-butyl ester for the L-proline tert-butyl ester in the procedure of Example 13, and then submitting the product to the procedures of Examples 14 and 15, N-[2-acetylthiomethyl-5-(p-methoxybenzyloxycarbonylamino)pentanoyl]-L-phenylalanine tert-butyl ester, N-[2-acetylthiomethyl-5-aminopentanoyl]-L-phenylalanine and N-(5-amino-2-mercaptomethylpentanoyl)-L-phenylalanine are obtained.

EXAMPLE 26

N-(5-Amino-2-mercaptomethylpentanoyl)-L-serine

By substituting O-tert-butyl L-serine tert-butyl ester for the L-proline tert-butyl ester in the procedure of Example 13, and then submitting the product to the procedures of Examples 14 and 15, N-[2-acetylthiomethyl-5-(p-methoxybenzyloxycarbonylamino)pentanoyl]-O-tert-butyl L-serine tert-butyl ester, N-(2-acetylthiomethyl-5-aminopentanoyl)-L-serine and N-(5-amino-2-mercaptomethylpentanoyl)-L-serine are obtained.

EXAMPLE 27

1-(5-Amino-2-mercaptomethylpentanoyl)-4-hydroxy-L-proline

By substituting 4-hydroxy-L-proline p-methoxybenzyl ester for the L-proline tert-butyl ester in the procedure of Example 13, and then submitting the product to the procedures of Examples 14 and 15, 1-[2-acetylthiomethyl-5-(p-methoxybenzyloxycarbonylamino)pentanoyl]-4-hydroxy-L-proline p-methoxybenzyl ester, 1-(2-acetylthiomethyl-5-aminopentanoyl)-4-hydroxy-L-proline, and 1-(5-amino-2-mercaptomethylpentanoyl)-4-hydroxy-L-proline are obtained.

EXAMPLE 28

1-(5-Amino-2-mercaptomethylpentanoyl)pipecolic acid

By substituting pipecolic acid tert-butyl ester (obtained from pipecolic acid by the procedure described for the synthesis of L-proline tert-butyl ester) for the L-proline tert-butyl ester in the procedure of Example 13 and then submitting the product to the procedure of Examples 14 and 15, 1-[2-acetylthiomethyl-5-(p-methoxybenzyloxycarbonylamino)pentanoyl]pipecolic acid tert-butyl ester, 1-(2-acetylthiomethyl-5-aminopentanoyl)pipecolic acid and 1-(5-amino-2-mercaptomethylpentanoyl)pipecolic acid are obtained.

EXAMPLE 29

$N^\alpha$-[2-Acetylthiomethyl-5-(p-methoxybenzyloxycarbonylamino)-pentanoyl]-L-arginine A solution of 2-acetylthiomethyl-5-(p-methoxybenzyloxycarbonylamino)pentanoic acid N-hydroxysuccinimide ester (4.6 g) in ethanol (16 ml) is added to a solution of L-arginine (1.47 g) in a mixture of water (15 ml) and sodium bicarbonate (1.68 g). The mixture is stirred at room temperature for 8 hours, acidified to pH 3 and extracted with ethyl acetate. The aqueous phase is applied to a column of Dowex 50 ion exchange resin (100 ml) in the hydrogen cycle. The column is washed with water until no more acidic material is eluted and then $N^\alpha$-[2-acetylthiomethyl-5-(p-methoxybenzyloxycarbonylamino)pentanoyl]-L-arginine is eluted with pyridine-acetate buffer at pH 6.5.

EXAMPLE 30

$N^\alpha$-(2-Acetylthiomethyl-5-aminopentanoyl)-L-arginine trifluoroacetate

A solution of $N^\alpha$-[2-acetylthiomethyl-5-(p-methoxybenzyloxycarbonylamino)pentanoyl]-L-arginine (1 g) in trifluoroacetic acid (10 ml) is stored at room temperature for 15 minutes, and then concentrated to dryness in vacuo to yield $N^\alpha$-(2-acetylthiomethyl-5-aminopentanoyl)-L-arginine trifluoroacetate.

EXAMPLE 31

$N^\alpha$-(5-Amino-2-mercaptomethylpentanoyl)-L-arginine $N^\alpha$-(2-acetylthiomethyl-5-aminopentanoyl)-L-arginine trifluoroacetate (2 g) is dissolved in a mixture of water (25 ml) and concentrated ammonia (25 ml) and this solution is stored at room temperature for 20 minutes. The solution is concentrated in vacuo to ca. 5 ml and applied to a column of Dowex 50 ion exchange resin (50 ml) in the hydrogen cycle. After washing with water $N^\alpha$-(5-amino-2-mercaptomethylpentanoyl)-L-arginine is eluted with a pyridine-acetate buffer at pH 6.5.

EXAMPLE 32

$N^\alpha$-[2-Acetylthiomethyl-5-(p-methoxybenzyloxycarbonylamino)pentanoyl]-$N^\epsilon$-tert-butyloxycarbonyl-L-lysine tert-butyl ester By substituting $N^\epsilon$-tert-butyloxycarbonyl lysine tert-butyl ester for the L-proline tert-butyl ester in the procedure of Example 13, $N^\alpha$-[2-acetylthiomethyl-5-(p-methoxybenzyloxycarbonylamino)pentanoyl]-$N^\epsilon$-tert-butyloxycarbonyl-L-lysine tert-butyl ester is obtained.

EXAMPLE 33

$N^\alpha$-(2-Acetylthiomethyl-5-aminopentanoyl)-L-lysine trifluoroacetate

A solution of $N^\alpha$-[2-acetylthiomethyl-5-(p-methoxybenzyloxycarbonylamino)pentanoyl]-$N^\epsilon$-tert-butyloxycarbonyl-L-lysine tert-butyl ester (1 g) in trifluoroacetic acid (5 ml) is stored at room temperature for 1 hour and then concentrated to dryness in vacuo to yield $N^\alpha$-(2-acetylthiomethyl-5-aminopentanoyl)-L-lysine trifluoroacetate.

EXAMPLE 34

$N^\alpha$-(5-Amino-2-mercaptomethylpentanoyl)-L-lysine

By substituting $N^\alpha$-(2-acetylthiomethyl-5-aminopentanoyl)-L-lysine trifluoroacetate for the $N^\alpha$-(2-acetylthiomethyl-5-aminopentanoyl)-L-arginine in the procedure of Example 31, $N^\alpha$-(5-amino-2-mercaptomethylpentanoyl)-L-lysine is obtained.

EXAMPLE 35

$N^\alpha$-(5-Amino-2-mercaptomethylpentanoyl)-L-histidine

By substituting L-histidine for the L-arginine in the procedure of Example 29 and then submitting the product to the procedures of Examples 30 and 31, $N^\alpha$-[2-acetylthiomethyl-5-(p-methoxybenzyloxycarbonylamino)pentanoyl]-L-histidine, $N^\alpha$-(2-acetylthiomethyl-5-aminopentanoyl)-L-histidine, and $N^\alpha$-(5-amino-2-mercaptomethylpentanoyl)-L-histidine are obtained.

EXAMPLE 36

N-(5-Amino-2-mercaptomethylpentanoyl)-L-methionine

By substituting L-methionine diphenylmethyl ester for the L-proline tert-butyl ester in the procedure of Example 13, and then submitting the product to the procedures of Examples 14 and 15, N-[2-acetylthiomethyl-5-(p-methoxybenzyloxycarbonylamino)pentanoyl]-L-methionine diphenylmethyl ester, N-(2-acetylthiomethyl-5-aminopentanoyl)-L-methionine, and N-(5-amino-2-mercaptomethylpentanoyl)-L-methionine are obtained.

EXAMPLE 37

N-[2-Acetylthiomethyl-5-(p-methoxybenzyloxycarbonylamino)-pentanoyl]-L-tryptophane methyl ester A solution of L-tryptophane methyl ester hydrochloride (2.5 g), 2-acetylthiomethyl-5-(p-methoxybenzyloxycarbonylamino)pentanoic acid N-hydroxysuccinimide ester (4.6 g), and hydroxybenzotriazole (1.35 g) in a mixture of dimethylformamide (20 ml) and triethylamine (1.6 ml) is stored at room temperature overnight. The solvent is removed in vacuo, the residue is dissolved in ethyl acetate and washed neutral. The organic phase is dried and concentrated to dryness to yield N-[2-acetylthiomethyl-5-(p-methoxybenzyloxycarbonylamino)pentanoyl]-L-tryptophane methyl ester.

EXAMPLE 38

N-(2-Acetylthiomethyl-5-aminopentanoyl)-L-tryptophane methyl ester trifluoroacetate N-[2-Acetylthiomethyl-5-(p-methoxybenzyloxycarbonylamino)pentanoyl]-L-tryptophane methyl ester (1 g) is dissolved in trifluoroacetic acid (10ml), the solution is stored at room temperature for 15 minutes, and then evaporated in vacuo to yield N-(2-acetylthiomethyl-5-aminopentanoyl)-L-tryptophane methyl ester trifluoroacetate.

EXAMPLE 39

N-(5-Amino-2-mercaptomethylpentanoyl)-L-tryptophane

To a solution of N-(2-acetylthiomethyl-5-aminopentanoyl)-L-tryptophane methyl ester trifluoroacetate (3 g) in methanol (60 ml) N sodium hydroxide (60 ml) is added. After 4 hours the solution is applied to a column of Dowex 50 ion exchange resin in the hydrogen cycle. After washing with water, the N-(5-amino-2-mercaptomethylpentanoyl)-L-tryptophane is eluted with pyridine-acetic acid buffer at pH 6.5.

EXAMPLE 40

N-(5-Amino-2-mercaptomethylpentanoyl)-L-glutamine

By substituting L-glutamine tert-butyl ester for the L-proline tert-butyl ester in the procedure of Example 13, and then submitting the product to the procedures of Examples 14 and 15, N-[2-acetylthiomethyl-5-(p-methoxybenzyloxycarbonylamino)pentanoyl]-L-glutamine tert-butyl ester, N-(2-acetylthiomethyl-5-aminopentanoyl)-L-glutamine, and N-(5-amino-2-mercaptomethylpentanoyl)-L-glutamine are obtained.

EXAMPLE 41

N-(5-Amino-2-mercaptomethylpentanoyl)-L-aspartic acid

By substituting L-aspartic acid di tert-butyl ester for the L-proline tert-butyl ester is the procedure of Example 13, and then submitting the product to the procedures of Examples 14 and 15, N-[2-acetylthiomethyl-5-(p-methoxybenzyloxycarbonylamino)pentanoyl]-L-aspartic di tert-butyl ester, N-(2-acetylthiomethyl-5-aminopentanoyl)-L-aspartic acid, and N-(5-amino-2-mercaptomethylpentanoyl)-L-aspartic acid are obtained.

EXAMPLE 42

D-Cysteinyl-L-alanine

By substituting L-alanine tert-butyl ester for the L-proline tert-butyl ester in the procedure of Example 1, and then submitting the product to the procedure of Example 2, D-cysteinyl-L-alanine is obtained.

EXAMPLE 43

D-Cysteinyl-L-phenylglycine

By substituting L-phenylglycine tert-butyl ester (prepared from L-phenylglycine by the procedure described for L-proline tert-butyl ester) for the L-proline tert-butyl ester in the procedure of Example 1, and then submitting the product to the procedure of Example 2, D-cysteinyl-L-phenylglycine is obtained.

EXAMPLE 44

D-Cysteinyl-L-threonine

By substituting O-tert-butyl-L-threonine tert-butyl ester for the L-proline tert-butyl ester in the procedure of Example 1 and then submitting the product to the procedure of Example 2, D-cysteinyl-L-threonine is obtained.

EXAMPLE 45

N-(5-Guanidino-2-mercaptomethylpentanoyl)-L-phenylalanine

By substituting N-(5-amino-2-mercaptomethylpentanoyl)-L-phenylalanine for the 1-(5-amino-2-mercaptomethylpentanoyl)-L-proline in the procedure of Example 22, N-(5-guanidino-2-mercaptomethylpentanoyl)-L-phenylalanine is obtained.

EXAMPLE 46

N-(5-Guanidino-2-mercaptomethylpentanoyl)-L-leucine

By substituting N-(5-amino-2-mercaptomethylpentanoyl)-L-leucine for the 1-(5-amino-2-mercaptomethylpentanoyl)-L-proline in the procedure of Example 22, N-(5-guanidino-2-mercaptomethylpentanoyl)-L-leucine is obtained.

EXAMPLE 47

3-Acetylthio-2-methoxycarbonylmethylpropanoic acid

A mixture of thiolactic acid (12.5 g) and 3-methoxycarbonyl-2-methylenepropanoic acid (17.1 g) are heated on the steam bath for 2 hours. The reaction is concentrated in vacuo and the residue is dissolved in ethyl acetate (125 ml) and dicyclohexylamine (35 ml) is added. The crystals are filtered, dried and recrystallized from ethyl acetate to yield 37.8 g, of the dicyclohexylammonium salt of 3-acetylthio-2-methoxycarbonylmethylpropanoic acid, m.p. 120°–121°. This dicyclohexylammonium salt is converted to the free acid, 3-acetylthio-2-methoxycarbonylmethylpropanoic acid, by distribution between ethyl acetate and 10% aqueous potassium bisulfate.

EXAMPLE 48

1-[3-(Acetylthio)-2-methoxycarbonylmethylpropanoyl]-L-proline tert-butyl ester

To a solution of L-proline tert-butyl ester (1.71 g) and 3-hydroxybenzotriazole (1.35 g) in dichloromethane (15 ml), dicyclohexylcarbodiimide (2.06 g) and 3-acetylthio-2-methoxycarbonylmethylpropanoic acid (2.2 g) are added. After 18 hours stirring at room temperature, the precipitate formed is filtered off, the filtrate is washed neutral, dried, and concentrated to dryness to yield 3.7 g of 1-[3-(acetylthio)-2-methoxycarbonylmethylpropanoyl]-L-proline tert-butyl ester. $R_f=0.8$ (silica gel-etyl acetate).

EXAMPLE 49

1-[3-(Acetylthio)-2-carboxymethylpropanoyl]-L-proline tert-butyl ester

To a solution of 1-[3-(acetylthio)-2-methoxycarbonylmethylpropanoyl]-L-proline tert-butyl ester (3.7 g) in methanol (60 ml), N sodium hydroxide (40 ml) is added. After 4 hours, the reaction mixture is diluted with water (100 ml) and extracted with ethyl acetate. The aqueous layer is acidified and extracted with ethyl acetate. This last ethyl acetate layer is dried and concentrated to dryness in vacuo. The residue is dissolved in a mixture of pyridine and acetic anhydride (3:1) and the solution is stored at room temperature overnight. The reaction mixture is diluted with ethyl acetate (200 ml) and washed with 10% potassium bisulfate. The organic layer is dried and concentrated to dryness in vacuo to yield 1-[3-(acetylthio)-2-carboxymethylpropanoyl]-L-proline tert-butyl ester.

EXAMPLE 50

1-[3-(Acetylthio)-2-tert-butyloxycarbonylaminomethylpropanoyl]-L-proline tert-butyl ester To a solution of 1-[3-(acetylthio)-2-carboxymethylpropanoyl]-L-proline tert-butyl ester (3.6 g) in tert-butanol (60 ml), triethylamine (1.4 ml) and diphenylphosphoryl azide (2.75 g) are added. The mixture is refluxed for 22 hours, and concentrated to dryness in vacuo. The residue is dissolved in ethyl acetate and the solution is washed neutral. The organic phase is dried and concentrated to dryness in vacuo to yield 1-[3-(acetylthio)-2-tert-butyloxycarbonylaminomethylpropanoyl]-L-proline tert-butyl ester.

EXAMPLE 51

1-(3-Acetylthio-2-aminomethylpropanoyl)-L-proline

1-[3-(acetylthio)-2-tert-butyloxycarbonylaminomethylpropanoyl]-L-proline-tert-butyl ester (1.5 g) is dissolved in a mixture of anisole (6 ml) and trifluoroacetic acid (12 ml) and the solution is stored at room temperature for 1 hour. The solvent is removed in vacuo, the residue is distributed between water and ether. The aqueous phase is washed twice with ether and freeze-dried to yield 1-(3-acetylthio-2-aminomethylpropanoyl)-L-proline.

EXAMPLE 52

1-(2-Aminomethyl-3-mercaptopropanoyl)-L-proline

By substituting 1-(3-acetylthio-2-aminomethylpropanoyl)-L-proline for the 1-(2-acetylthiomethyl-5-aminopentanoyl)-L-proline trifluoroacetate in the procedure of Example 15, 1-(2-aminomethyl-3-mercaptopropanoyl)-L-proline is obtained.

EXAMPLE 53

1-(5-Guanidino-2-mercaptomethylpentanoyl)pipecolic acid

By substituting 1-(5-amino-2-mercaptomethylpentanoyl)-pipecolic acid for the 1-(5-amino-2-mercaptomethylpentanoyl)-L-proline in the procedure of Example 22, 1-(5-guanidino-2-mercaptomethylpentanoyl)-pipecolic acid is obtained.

EXAMPLE 54

1-(5-Guanidino-2-mercaptomethylpentanoyl)-4-hydroxy-L-proline

By substituting 1-(5-amino-2-mercaptomethylpentanoyl)-4-hydroxy-L-proline for the 1-(5-amino-2-mercaptomethylpentanoyl)-L-proline in the procedure of Example 22, 1-(5-guanidino-2-mercaptomethylpentanoyl)-4-hydroxy-L-proline is obtained.

EXAMPLE 55

1,1'-Dithiobis-(2-D-amino-3-propanoyl)-bis-L-proline

An alcoholic solution of iodine is added dropwise to a solution of D-cysteine-L-proline (1 g.) in water (10 ml.) while keeping the pH between 5 and 7 by careful addition of N sodium hydroxide. When a persistant yellow color is obtained, the solution is applied to a column of Dowex 50 ion exchange resin in the hydrogen cycle and washed with water. The 1,1'-dithiobis-(2-D-amino-3-propanoyl)-bis-L-proline is eluted with a pyridine-buffer at pH 6.5.

EXAMPLE 56

1-[2-Mercaptomethyl-5-(p-methoxybenzyloxycarbonylamino)-pentanoyl]-L-proline

By substituting 1-[2-acetylthiomethyl-5-(p-methoxybenzyloxycarbonylamino)pentanoyl]-L-proline for the N,S-diacetyl-DL-cysteinyl-L-proline in the procedure of Example 5, 1-[2-mercaptomethyl-5-(p-methoxybenzyloxycarbonylamino)pentanoyl]-L-proline is obtained.

EXAMPLE 57

1,1'-Dithiobis-[2-(p-methoxybenzyloxycarbonylaminopropyl)-3-propanoyl]-bis-L-proline By substituting 1-[2-mercaptomethyl-5-(p-methoxybenzyloxycarbonylamino)pentanoyl]-L-proline for the D-cysteinyl-L-proline in the procedure of Example 55, 1,1'-dithiobis-[2-(p-methoxybenzyloxycarbonylaminopropyl)-3-propanoyl]-bis-L-proline is obtained.

EXAMPLE 58

1,1'-Dithiobis-(2-aminopropyl-3-propanoyl)-bis-L-proline

By substituting 1,1'-dithiobis-[2-(p-methoxybenzyloxycarbonylaminopropyl)-3-propanoyl]-bis-L-proline for the $N^\alpha$-[2-acetylthiomethyl-5-(p-methoxybenzylcarbonylamino)pentanoyl]-L-arginine in the procedure of Example 30, 1,1'-dithiobis-(2-aminopropyl-3-propanoyl)-bis-L-proline is obtained.

EXAMPLE 59

1,1'-Dithiobis-(2-aminopropyl-3-propanoyl)-bis-L-leucine

By substituting N-(5-amino-2-mercaptomethylpentanoyl)-L-leucine for the D-cysteine-L-proline in the procedure of Example 55, 1,1'-dithiobis-(2-aminopropyl-3-propanoyl)-bis-L-leucine is obtained.

EXAMPLE 60

L-Cysteinyl-L-proline acetate

By substituting N-tert-butyloxycarbonyl-S-p-methoxybenzyl-L-cysteine for the N-tert-butyloxycarbonyl-S-p-methoxybenzyl-D-cysteine in the procedure of Example 1 and submitting the product to the procedure of Example 2, N-tert-butyloxycarbonyl-S-p-methoxybenzyl-L-cysteinyl-L-proline tert-butyl ester and L-cysteinyl-L-proline acetate are obtained.

What is claimed is:

1. A compound of the formula

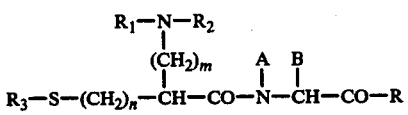

and salts physiologically acceptable thereof, wherein

R is hydroxy or lower alkoxy $R_1$ is hydrogen, lower alkanoyl or amino (imino)methyl;

$R_2$ is hydrogen, lower alkyl or phenyl-lower alkylene;

$R_3$ is hydrogen, lower alkanoyl, benzoyl or

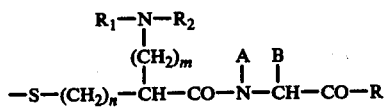

A and B together form a $(CH_2)_p$ bridge which completes an unsubstituted ring of 5 atoms with the nitrogen and carbon to which they are joined or said ring substituted with a hydroxy group;

m is 1, 2, 3, or 4;

n is 0 or 1; and p is 3.

2. A compound of the formula

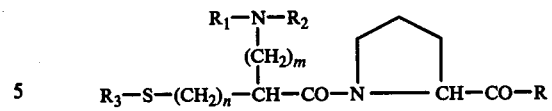

and salts thereof, wherein R, $R_1$, $R_2$, $R_3$, m and n have the same meaning as in claim 1.

3. A compound as in claim 1 wherein R is hydroxy; $R_1$ is hydrogen, lower alkanoyl, or amino (imino)methyl; $R_2$ is hydrogen, lower alkyl or phenyl-lower alkylene; $R_3$ is hydrogen, lower alkanoyl or benzoyl; m is 3 or 4 and n is 0 or 1.

4. A compound as in claim 1 wherein $R_3$ is

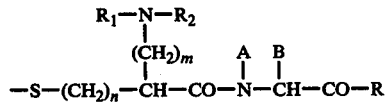

5. A compound as in claim 2 wherein R, $R_1$, $R_2$, $R_3$, m and n have the same meanings as in claim 3.

6. A compound as in claim 1 wherein R is hydroxy.

7. A compound as in claim 2 wherein R is hydroxy.

8. A compound as in claim 2 wherein R is hydroxy and $R_1$, $R_2$ and $R_3$ each is hydrogen.

9. A compound as in claim 2 wherein R is hydroxy, $R_1$, $R_2$ and $R_3$ each is hydrogen, m is 3 and n is 1.

10. A compound as in claim 2 wherein R is hydroxy, $R_2$ and $R_3$ each is hydrogen, $R_1$ is amino (imino)methyl, m is 3 and n is 1.

11. 1-(5-Guanidino-2-mercaptomethylpentanoyl)-4-hydroxy-L-proline.

* * * * *

UNITED STATES PATENT AND TRADEMARK OFFICE
CERTIFICATE OF CORRECTION

PATENT NO. : 4,129,571
DATED : December 12, 1978
INVENTOR(S) : Miguel Angel Ondetti, Michael E. Condon It is certified that error appears in the above-identified patent and that said Letters Patent are hereby corrected as shown below:

Column 3, Formula (VI) "$(CH_2)_m$———— N" should read
-- $(CH_2)_m$———— NH --
Column 13, line 43, "is" should read -- in --
Column 17, Claim 1, line 8 "physiologically acceptable" should be inserted before "salts" rather than after it Signed and Sealed this Twenty-fourth Day of April 1979

[SEAL]

Attest:

RUTH C. MASON
Attesting Officer

DONALD W. BANNER
Commissioner of Patents and Trademarks